United States Patent [19]

Schröder et al.

[11] 4,199,572

[45] Apr. 22, 1980

[54] N-SUBSTITUTED AMINO GLYCOSIDE COMPOUNDS, THEIR PRODUCTION, AND THEIR USE AS MEDICAMENTS

[75] Inventors: Theo Schröder; Karl-Georg Metzger, both of Wuppertal, Fed. Rep. of Germany

[73] Assignee: Bayer Aktiengesellschaft, Leverkusen, Fed. Rep. of Germany

[21] Appl. No.: 881,263

[22] Filed: Feb. 24, 1978

[30] Foreign Application Priority Data

Mar. 19, 1977 [DE] Fed. Rep. of Germany ........ 2712160

[51] Int. Cl.² ........................ A61K 31/71; C07H 15/22
[52] U.S. Cl. ...................................... 424/180; 536/10; 536/17 R
[58] Field of Search ...................... 536/10, 17; 424/180

[56] References Cited

U.S. PATENT DOCUMENTS

| 3,920,628 | 11/1975 | Daniels | 536/17 |
| 4,002,608 | 1/1977 | Wright et al. | 536/17 |
| 4,002,742 | 1/1977 | Wright et al. | 536/17 |
| 4,062,947 | 12/1977 | Wright et al. | 536/17 |
| 4,085,208 | 4/1978 | Mallams et al. | 536/17 |

Primary Examiner—Johnnie R. Brown
Attorney, Agent, or Firm—Sprung, Felfe, Horn, Lynch & Kramer

[57] ABSTRACT

The invention relates to new derivatives, substituted on one or more nitrogen atoms, of 4,6-di-(amino-glycosyl)-1,3-diamino-cyclitols, which include the gentamycins, sisomicin, verdamycin, tobramycin, the kanamycins, the antibiotics G-418, 66-40 B, 66-40 D, JI-20 B, JI-20 B and G-52, and the 5-epi-, 5-epi-amino-5-deoxy and 5-epi-azido-5-deoxy derivatives of these antibiotics and the metamycins, and furthermore to processes for the preparation of these derivatives and to pharmaceutical compositions which contain the derivatives of the above mentioned 4,6-di-(amino-glycosyl)-1,3-diamino-cyclitols or their pharmaceutically acceptable acid addition salts, and to their use as antibacterial agents.

28 Claims, No Drawings

N-SUBSTITUTED AMINO GLYCOSIDE COMPOUNDS, THEIR PRODUCTION, AND THEIR USE AS MEDICAMENTS

The present invention relates to certain new N-substituted compounds, processes for their production and to their use as medicaments.

In particular, the invention relates to new derivatives, substituted on one or more nitrogen atoms, of 4,6-di(amino-glycosyl)-1,3-diamino-cyclitols, which include the gentamycins, sisomicin, verdamycin, tobramycin, the kanamycins, the antibiotics G-418, 66-40 B, 66-40 D, JI-20 A, JI-20 B and G-52, and the 5-epi-, 5-epi-amino-5-deoxy and 5-epi-azido-5-deoxy derivatives of these antibiotics and the mutamycins, and furthermore to processes for the preparation of these derivatives and to pharmaceutical compositions which contain the derivatives of the above mentioned 4,6-di-(aminoglycosyl)-1,3-diaminocyclitols or their pharmaceutically acceptable acid addition salts, and to their use as antibacterial agents.

The above mentioned unsubstituted 4,6-di-(amino-glycosyl)-1,3-diaminocyclitol antibiotics have been described as good antibacterial agents. Nitrogen containing antibacterial agents substituted on the nitrogen have also been disclosed.

It has now been found that valuable new antibiotics are obtained when a hydrogen atom in one or more amino groups of a 4,6-di-(aminoglycosyl)-1,3-diaminocyclitol is replaced by a substituent of the general formula

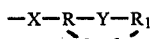  (I)

wherein X, Y, R and $R_1$ have the meanings defined hereinbelow.

The compounds of the invention are derivatives, substituted on one or more, preferably on one, two or three, nitrogen atoms, of the 4,6-di-(amino-glycosyl)-1,3-diamino-cyclitol antibiotics sisomicin, verdamycin, tobramycin, the kanamycins, the gentamycins A, B, $B_1$, $C_1$, $C_{1a}$, $C_2$, $C_{2a}$, $C_{2b}$ and $X_2$, the antibiotics G-418, 66-40 B, 66-40 D, JI-20 A, JI-20 B and G-52, as well as their 5-epi, 5-epi-amino-5-deoxy and 5-epi-azido-5-deoxy derivatives, and the mutamycins 1, 2, 4, 5 and 6, by a substituent of the general formula

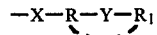  (I)

wherein X, Y, R and $R_1$ have the meanings defined hereinbelow.

The compounds according to the invention, with the exception of mutamycins, contain 2-deoxystreptamine. The 1,3-diaminocyclitol ring in the derivatives of mutamycin 1, 2, 4, 5 and 6 is, respectively, streptamine, 2,5-dideoxystreptamine, 2-epi-streptamine, 5-amino-2,5-dideoxystreptamine and 5-epi-2-deoxystreptamine.

In formula I,
X is a divalent radical —$CH_2$— or >CO, which leads from a N atom of the 4,6-di-(amino-glycosyl)-1,3-diaminocyclitol ring to a C atom of R; and
when R is not bonded to $R_1$, Y is oxygen or sulphur;
R is an optionally substituted alkylene radical; and
$R_1$ is optionally substituted alkyl, optionally substituted alkenyl, optionally substituted cycloalkyl, optionally substituted cycloalkylalkyl, optionally substituted aralkyl, optionally substituted aryl or optionally substituted heterocyclic, optionally linked to Y via a methylene bridge, or
when R is bonded to $R_1$,

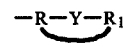

together represent an optionally substituted heterocyclic ring containing 1 or 2 hetero-atoms. R preferably is an optionally substituted alkylene radical having from 1 to 6 C atoms.

Preferred substituents of the alkylene radical which may be mentioned are: alkyl, having preferably from 1 to 8 C atoms, optionally substituted by halogen, preferably Cl, Br or F, nitro, hydroxyl, amino, R'—O—, R'—S—, R'—NH—, (R')$_2$—N—, R'—CO—NH— or (R'CO)$_2$—N—, wherein R' is an alkyl radical having preferably from 1 to 4 C atoms, or alkenyl, having preferably from 2 to 8 C atoms; cycloalkyl, having preferably from 3 to 10 C atoms; cycloalkylalkyl, preferably cycloalkylmethyl or cycloalkylethyl; aryl, preferably phenyl; arylalkyl, preferably benzyl; a heterocyclic radical, preferably the radical of a 5-membered or 6-membered heterocyclic ring, optionally linked to the alkylene radical via a methylene group; alkoxy, having preferably from 1 to 6 C atoms; alkylthio, having preferably from 1 to 6 C atoms; and alkylamino, dialkylamino, acylamino or diacylamino, preferably having from 1 to 4 C atoms in the alkyl or acyl moiety in each case.

Examples of suitable substituents of the alkylene radical are: methyl, ethyl, n-propyl, i-propyl, n-butyl, i-butyl, tert.-butyl, 1-methylpropyl, n-pentyl, 1- and 2-methylbutyl, 3-methylbutyl and 1,1- and 2,2-dimethylpropyl, n-hexyl, 4-methylpentyl, 1- and 2-ethylbutyl, 3-ethylbutyl, n-heptyl, 5-methylheptyl, 1- and 2-ethylpentyl, 3-ethylbutyl, n-heptyl, 5-methylheptyl, 1- and 2-ethylpentyl, 3-ethylpentyl, 4-ethylpentyl, 3-propylbutyl, n-octyl, iso-octyl, 1- and 2-ethylhexyl, 4-ethylhexyl, 5-ethylhexyl, 2-propylpentyl, 3-propylpentyl, alkenyl, for example, vinyl, 1- and 2-propenyl, 1- and 2-methylpropenyl, 2-butenyl, 2-methyl-2-butenyl and 2-ethyl-2-hexenyl, a cyclic group, for example, cyclopropyl, cyclopropylmethyl, cyclopentyl, cyclopentylmethyl, cyclohexyl, cyclohexylmethyl, cyclopentylethyl and cyclohexylethyl, an aromatic group, for example, phenyl, benzyl and o-, m- and p-methylbenzyl, a heterocyclic radical for example, pyridyl, pyrryl, furyl, furfuryl, thiophenyl, morpholinyl or piperidinyl, straight-chain and branched alkyl substituted by hydroxyl, for example, 3-hydroxypentyl, 2-hydroxy-3-methyl-butyl, 2-hydroxy-2-methyl-propyl, 1-, 2-, 3- and 4-hydroxybutyl, 2- and 3-hydroxypropyl and 8-hydroxyoctyl, straight-chain alkyl substituted by amino, for example, 1-, 2-, 3-, 4- and 5-aminopentyl, 2- and 3-aminopropyl, 4-aminobutyl, 2-aminobutyl, 2-amino-3-methylbutyl and 8-aminooctyl and their monoalkylated and di-N-alkylated derivatives, such as their N-methyl, N,N-dimethyl-, N-ethyl- and N-propyl derivatives, for example 5-methylaminopentyl, 2-methyl-aminopropyl, 2-ethylaminopropyl, 4-methylaminobutyl, 2-methylamino-3-methylbutyl and 4-methylaminobutyl, straight-chain and branched alkyl substituted by amino and hydroxyl, for example, 1- and 2-hydroxy-5-aminopentyl, 3-hydroxy-3-methyl-4-aminobutyl, 2-hydroxy-4-amino-butyl, 2-hydroxy-3-aminopropyl and 2-hydroxy-2-methyl-3-amino-propyl- and their mono-N- alkylated derivatives, for example 2-hydroxy-5-methylaminopentyl, 3-hydroxy-3-methyl-4-methylaminobutyl, 2-hydroxy-4-methylaminobutyl, 2-hydroxy-3-ethyl-aminopropyl and 2-hydroxy-2-methyl-3-methylaminopropyl; and straight-chain and branched alkyl substituted by alkoxy, for example, methoxymethyl, ethoxymethyl, n- and i-propoxymethyl, n, i- and tert.-butoxymethyl, methoxyethyl, ethoxyethyl, 3-methoxypropyl, 3-ethoxypropyl, 2-methoxypropyl and 2-ethoxypropyl.

However, R particularly preferably denotes a methylene or a di-, tri-, tetra-, penta- or hexa-methylene radical, which can be substituted by one or more alkyl radicals having from 1 to 4 C atoms, preferably 1 or 2 C atoms. Examples of suitable radicals of this type are:

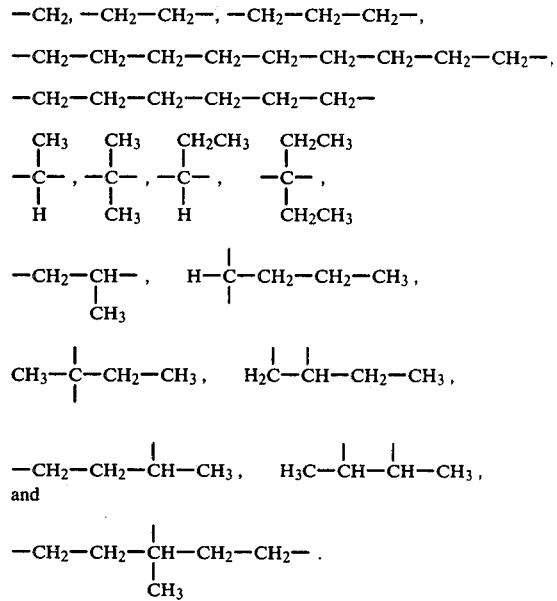

$R_1$ preferably is optionally substituted alkyl having from 1 to 8 C atoms, optionally substituted alkenyl having from 2 to 8 C atoms, optionally substituted cycloalkyl having from 3 to 10 C atoms, optionally substituted cycloalkylmethyl or cycloalkylethyl radical having from 3 to 10 C atoms in the cycloalkyl moiety, optionally substituted phenyl, naphthyl or benzyl or an optionally substituted 5-membered to 7-membered hetero-cyclic radical, optionally linked to Y via a methylene bridge.

Possible substituents for the radicals mentioned are preferably one or more identical or different substituents each of which is hydroxyl, amino, mercapto, halogen, preferably Cl, Br or F, nitro, alkoxy having from 1 to 6 C atoms or alkylthio having from 1 to 6 C atoms; or alkylamino, dialkylamino, acylamino or diacylamino having from 1 to 4 C atoms in the alkyl or acyl moiety in each case. $R_1$ can have, for example, any of the following meanings: straight-chain and branched alkyl, for example methyl, ethyl, n- and i-propyl, n-, i- and tert.-butyl, 1-methylpropyl, n-pentyl, 1- and 2-methylbutyl, 3-methylbutyl and 1,1- and 2,2-dimethylpropyl, n-hexyl, 4-methylpentyl, 1- and 2-ethylbutyl, 3-ethylbutyl, n-heptyl, 5-methylheptyl, 1- and 2-ethylpentyl, 3-ethylpentyl, 4-ethylpentyl, 3-propylbutyl, n-octyl, isooctyl, 1- and 2-ethylhexyl, 4-ethylhexyl, 5-ethylhexyl, 2-propylpentyl and 3-propylpentyl; alkenyl groups, such as, for example, vinyl, 1- and 2-propenyl, 1- and 2-methyl- propenyl, 2-butenyl, 2-methyl-2-butenyl and 2-ethyl-2-hexenyl; a cyclic group, for example, cyclopropyl, cyclopropyl-methyl, cyclopentyl, cyclopentylmethyl, cyclohexyl and cyclopentylethyl, an aromatic group for example, phenyl, benzyl and o-, m- and p-methylbenzyl, a heterocyclic radical, for example, pyridyl, pyrryl, furyl, furfuryl, thiophenyl, morpholinyl or piperidinyl; straight-chain and branched alkyl group substituted by hydroxyl for example, 3-hydroxypentyl, 2-hydroxy-3-methyl-butyl, 2-hydroxy-2-methylpropyl, 1,2- and 3-hydroxybutyl, 1- and 2-hydroxy-propyl, 3-hydroxypropyl and 8-hydroxyoctyl; straight-chain and branched alkyl substituted by amino, for example, 1-, 2-, 3-, 4- and 5-aminopentyl, 2- and 3-amino-propyl, 4-aminobutyl, 2-aminobutyl, 2-amino-3-methylbutyl and 8-aminooctyl, and their mono- and di-N-alkylated derivatives, such as their N-methyl, N,N-dimethyl, N-ethyl and N-propyl derivatives, for example 4-methylaminopentyl, 2-methyl-aminopropyl, 2-ethyl-aminopropyl, 4-methylaminobutyl, 2-methylamino-3-methylbutyl and 4-methylaminobutyl, straight-chain and branched alkyl substituted by amino and hydroxyl, for example, 1- and 2-hydroxy-5-aminopentyl, 3-hydroxy-3-methyl-4-aminobutyl, 2-hydroxy-4-aminobutyl, 2-hydroxy-3-aminopropyl and 2-hydroxy-2-methyl-3-aminopropyl; and their mono-N-alkylated derivatives, for example, 2-hydroxy-5-methylaminopentyl, 3-hydroxy-3-methyl-4-methylaminobutyl, 2-hydroxy-4-methylaminobutyl, 2-hydroxy-3-ethylaminopropyl and 2-hydroxy-2-methyl-3-methylaminopropyl; and straight-chain and branched alkyl substituted by alkoxy, for example, methoxymethyl, ethoxymethyl, n- and i-propoxymethyl, n-, i- and tert.-butoxymethyl, methoxyethyl, ethoxyethyl, 3-methoxypropyl, 3-ethoxypropyl, 2-methoxypropyl and 2-ethoxypropyl.

Those derivatives of 4,6-di-(aminoglycosyl)-1,3-diaminocyclitols in which $R_1$ is alkyl having from 1 to 4 C atoms, optionally substituted by alkoxy having from 1 to 4 C atoms, cycloalkyl, cycloalkylmethyl or cycloalkylethyl, having from 3 to 6 C atoms in the cycloalkyl moiety, or phenyl, benzyl, furyl, furylmethyl, pyranyl, pyranylmethyl, thienyl, thienylmethyl, tetrahydrofuryl, tetrahydrofurylmethyl or pyridyl, are particularly preferred.

In the case where R is bonded to $R_1$,

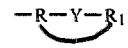

together represent a heterocyclic ring, which is preferably a 5- to 7-membered heterocyclic ring, preferably having from 1 to 3 substituents, for example, Cl, Br, $C_1$ to $C_4$-alkyl, $C_1$ to $C_4$-alkoxy, OH, SH, $C_1$ to $C_4$-alkylthio, $NH_2$, $C_1$ to $C_4$-monoalkylamino and $C_1$ to $C_4$-dialkylamino, and which heterocyclic ring contains one or two hetero atoms, preferably at least one O or S atom, and when the ring contains two hetero atoms, the second atom being preferably an N atom.

Preferred heterocyclic rings are: furyl, tetrahydrofuryl, chlorofuryl, bromofuryl, methylfuryl, pyranyl, morpholinyl, thienyl, chlorothienyl, bromothienyl and methylthienyl.

Specific examples which may be mentioned are: furyl-2, thien-2-yl, tetrahydrofuryl-3, 5-chlorofuryl-2, 5-bromofuryl-2, 5-methylfuryl-2, pyran-2-yl and morpholin-4-yl.

In the scope of this invention, those antibiotics which are substituted on one or more nitrogen atoms, but preferably on one nitrogen atom, by a substituent of general formula (I) as defined hereinbefore, and contain garosaminyl as the 6-aminoglycosyl radical and, preferably, contain 2-deoxystreptamine as the 1,3-diaminocylitol, such as, for example, gentamycin B, $B_1$, $C_1$, $C_{1a}$, $C_2$, $C_{2a}$, $C_{2b}$ and $X_2$, and antibiotics JI-20 A, JI-20 B and G-418, and their 5-epi, 5-epi-amino-5-deoxy and 5-epi-azido-5-deoxy derivatives are of particular importance.

The derivatives, substituted on one or more nitrogen atoms by said substituent of formula I, of verdamycin and of the antibiotics G-52 and 66-40 B and D are particularly preferred compounds according to the invention, and those of sisomicin, the structures of which are represented by the following general formula II, and their 5-epi, 5-epi-amino-5-deoxy and 5-epi-azido-5-deoxy derivatives most particularly preferred.

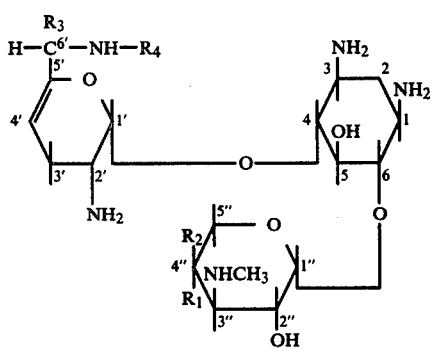
(II)

In formula II, $R_1$, $R_2$, $R_3$ and $R_4$ have the following meanings:

|  | $R_1$ | $R_2$ | $R_3$ | $R_4$ |
|---|---|---|---|---|
| for sisomicin | $CH_3$ | OH | H | H |
| for verdamycin | $CH_3$ | OH | $CH_3$ | H |
| for antibiotic 66-40B | OH | H | H | H |
| for antibiotic 66-40D | H | OH | H | H |
| for antibiotic G-52 | $CH_3$ | OH | H | $CH_3$ |

The compounds represented by the general formula II and their 5-epi, 5-epi-amino-5-deoxy and 5-epi-azido-5-deoxy derivatives in which a hydrogen atom in one or more of the amino groups on the carbon atoms designated 1, 3, 2′, 6′ and 3″ is replaced by a said substituent of formula I as defined hereinbefore, are compounds according to the invention.

Particularly valuable compounds according to the invention are represented by the formula III

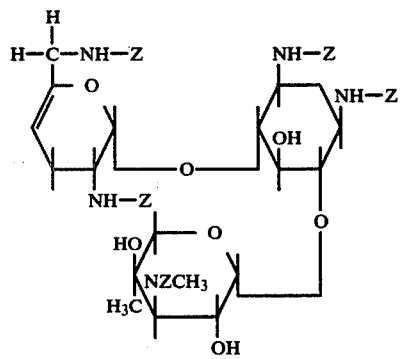
(III)

wherein in each case Z is hydrogen or a substituent of the general formula I, as defined hereinbefore, provided that at least one Z is not hydrogen. These compounds are sisomicin derivatives. Those derivatives with 1, 2 or 3 of said substituents of formula I are preferred, those having one said substituent of formula I on any one of the five N atoms being of particular importance.

In the case of compounds of formula III, the following meaning are preferred for X, R and $R_1$ when Z is a substituent of the general formula I: X is $-CH_2-$, and when R is not bonded to $R_1$, R is methylene or di-, tri-, tetra-, penta- or hexa-methylene, optionally substituted by alkyl having from 1 to 4 C atoms, and $R_1$ is alkyl having from 1 to 4 C atoms, optionally substituted by alkoxy having from 1 to 4 C atoms, cycloalkyl, cycloalkylmethyl or cycloalkylethyl having from 3 to 6 C atoms in the cycloalkyl moiety or phenyl, benzyl, furyl, furylmethyl, pyranyl, pyranylmethyl, thienyl, thienylmethyl, tetrahydrofuryl, tetrahydrofurylmethyl or pyridyl, or when R is bonded to $R_1$,

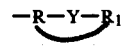

together represent furyl, tetrahydrofuryl, chlorofuryl, bromofuryl, methylfuryl, pyranyl or morpholinyl.

Particularly valuable sisomicin derivatives according to the present invention are those in which
X is $-CH_2-$ or $-CO-$, and
when R is not bonded to $R_1$, R is methylene, ethylene or trimethylene optionally substituted by from 1 to 3 methyl groups,
Y is O or S, and
$R_1$ is alkyl having from 1 to 4 C atoms, optionally substituted by methoxy, ethoxy, or phenyl, or when R is bonded to $R_1$,

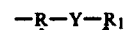

together represent furyl-2-, 5-methyl-, 5-chloro or 5-bromo-furyl-2-, or 5-methyl-, 5-chloro- or 5-bromothien-2-yl.

Particularly valuable derivatives are, for example, 1-N[2-methoxy-ethyl]-sisomicin, 1-[2-ethoxyethyl]-sisomicin, 1-[2-(n-propoxy)-ethyl]-sisomicin, 1-N[2-(2-methylthio)propyl]-sisomicin, 3″-N-[2-(n-butoxy)ethyl]-sisomicin, 1-N[2-(i-propoxy)ethyl-]-sisomicin, 1-N[2-(2,2-dimethyl-2-methoxy)-ethyl]-sisomicin, 1-N-[2-methoxyacetyl]-sisomicin, 6′-N-[2-ethoxyacetyl]-sisomicin and 1-N-[2-methylthioacetyl]-sisomicin.

Among the new salts of the invention, those salts that are pharmaceutically acceptable are particularly important and preferred.

The derivatives of the invention in the form of free bases and their salts can be interconverted in any suitable manner; methods for such interconversion are known in the art, for example the free base can be neutralised with the desired acid down to a pH value of from 4 to 5. Suitable acids are, for example, hydrochloric, sulphuric, phosphoric, nitric, hydrobromic, acetic, propionic, maleic, ascorbic and citric acid and the like. The acid addition salts of the invention are in general colourless solids which are soluble in water and most of the polar organic solvents.

The compounds of the invention, in which X is =CO, i.e. in which the substituent(s) of formula I is a substituent(s) of formula IV

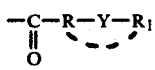 (IV)

wherein R, Y and $R_1$ have the same meaning as defined hereinbefore are also valuable intermediates for the preparation of the corresponding compounds in which X is —$CH_2$—, i.e. in which the substituent(s) of formula I is/are substituent(s) of formula V

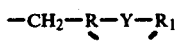 (V)

in which R, Y and $R_1$ have the same meaning as defined hereinbefore since they can be easily converted into the latter by reduction in a manner which is in itself known.

In a further aspect the present invention provides a process for the production of a compound of the invention in which a said antibiotic or derivative thereof, optionally containing one or more amino protective and/or hydroxy protective groups, according to how many substituents of formula (I) as defined hereinbefore are to be introduced, is reacted.

(a) with an acid of the general formula VII

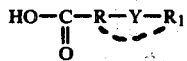 (VII)

in which

R, Y and $R_1$ have the same meaning as defined hereinbefore in formula (I) or a reactive derivative thereof which is an ester, azide, imidazole derivative, anhydride or chloride, in the presence of a carbodiimide so as to produce a said compound in which X is >CO;

(b) when X is methylene, with an aldehyde of the general formula

 (VI)

in which

R, Y and $R_1$ have the same meaning as defined hereinbefore in formula (I) in the presence of a hydrogen donor reducing agent;

(c) when X is methylene, with an aldehyde of the general formula VI

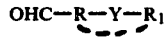 (VI)

in which

R, Y and $R_1$ have the same meaning as defined hereinbefore in formula (I) so as to produce a Schiff's base, which base is then reduced so as to produce said compound in which X is methylene;

(d) when X is a methylene group, with a reactive alkylating agent of the general formula VIII

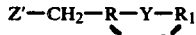 (VIII)

in which

Z' is a group which can be easily split off, and
R, Y and $R_1$ have the same meaning as defined hereinbefore in formula (I), so as to produce said compound in which X is methylene; or (e) when X is a methylene group, reducing a corresponding compound in which X is —CO— so as to produce said compound in which X is methylene; and
where one or more amino- or hydroxy- protective groups has been used, said protective group(s) is/are removed; and where a mixture of two or more compounds is obtained, optionally fractionating said mixture; and
where the compound is obtained in the form of a free base or an acid addition salt thereof, said compound is optionally converted into an acid addition salt or the corresponding free base, respectively.

The preparation of the starting antibiotics mentioned and of their 5-epi, 5-epi-amino-5-deoxy and 5-epi-azido-5-deoxy derivatives is known (see, for example, DOS (German Published Specification) 2,437,160 and DOS (German Published Specification) 2,552,799).

It will be appreciated that in general several different derivatives substituted on one or more different nitrogen atoms are usually obtained by a process of the invention. In this case the mixture of derivatives obtained may be fractionated by conventional fractionation methods such as, for example, liquid/liquid partition, extraction or a chromatographic process, such as, for example, silica gel, dextran gel or ion exchange chromatography. On the other hand the mixture of derivatives may themselves be used in medicine without further fractionation if desired.

In the case of process variant (b) described above, the reaction is usually carried out at room temperature or at an elevated temperature, for example, at the reflux temperature, and it can sometimes be advantageous to carry out the reaction in an inert gas atmosphere (argon or nitrogen). Even at room temperature the reaction is usually completed very rapidly, frequently in less than 30 minutes. However, it can also be advantageous to heat the mixture at least briefly to the reflux temperature.

Suitable hydrogen donor reducing agents which may be used in this process include dialkylaminoboranes (for example dimethylaminoborane, diethylaminoborane) and, preferably, morpholinoborane, tetraalkylammonium cycanoborohydrides (for example tetrabutylammonium cycanoborohydride), alkali metal borohydrides (for example sodium borohydride) and, preferably, alkali metal cyanoborohydrides (for example lithium cyanoborohydride and sodium cyanoborohydride).

The process is usually carried out in an inert solvent. The solvent can be an organic or inorganic solvent in which the 4,6-di-(aminoglycosyl)-1,3-diaminocyclitol and the other reactants are soluble and which as far as possible suppresses or prevents side reactions under the reaction conditions. Although it is possible to use anhydrous aprotic solvents (for example tetrahydrofurane, if the reducing agent is morpholinoborane), a protic solvent is usually employed. Suitable protic solvents are, for example, a lower alkanol or, preferably, water or an aqueous lower alkanol (for example aqueous methanol, ethanol, propanol or isopropanol) or other aqueous solvent systems, such as, for example, aqueous dimethylformamide, aqueous hexamethylphosphoric acid triamide, aqueous tetrahydrofurane or aqueous ethylene glycol dimethyl ether.

The process is usually carried out at a pH of from 1 to 11.

Since the proportions of the 4,6-di-(aminoglycosyl)-1,3-diaminocyclitols mono- and poly- substituted by said substituent of formula V, formed can be influenced by the pH of the reaction solution, the most favourable pH value for the formation of a particular desired product may be ascertained before carrying out large scale production, by varying the pH of the reaction medium and then monitoring the resulting products, for example, by determination by thin layer chromatography. Thus, for example, in the case of a procedure according to Example 1 hereinbelow using pH 7, ≈15% of 1-N-[2-(2-ethoxy-ethoxy)]-ethyl-sisomycin is formed, whilst when pH 10, is used only just about 2% of 1-N[2-ethoxy-ethoxy)]-ethylsisomycin is obtained. Thus in this case, in order to obtain a higher yield of 1-N[2-ethoxy-ethoxy)]-ethyl-sisomycin, a pH value of 7 is preferred.

The adjustment to the desired pH value may be achieved by adding an organic or inorganic acid or base to the 4,6-di(aminoglycosyl)-1,3-diaminocyclitol. When acids are added, the acid addition salt forms. Examples of suitable acids are acetic, trifluoroacetic, p-toluenesulphonic, hydrochloric, sulphuric, phosphoric and nitric acid. Sulphuric acid is preferably used. In a preferred embodiment of the process, the acid addition salt is formed in situ by adding the desired acid (for example sulphuric acid) to a solution or suspension of the 4,6-di-(aminoglycosyl)-1,3-diaminocyclitol (for example sisomycin) in a protic solvent (for example water) until the desired pH is reached.

Bases which can be used are all the inorganic and organic bases. Examples which may be mentioned are alkali metal hydroxide solution, such as sodium hydroxide solution, potassium hydroxide solution; $C_1$–$C_{12}$, preferably $C_1$–$C_4$ trialkyl amines, such as triethylamine or N-heterocyclic amines, such as pyridine. The aldehydes used in the process are either known or can easily be prepared by standard processes. Examples of typical aldehydes of the general formula VI which can be used in the process are: methoxy-acetaldehyde, ethoxy-acetaldehyde, n-propoxy-acetaldehyde, i-propoxy-acetaldehyde, n-butoxy-acetaldehyde, i-butoxy-acetaldehyde, tert.-butoxy-acetaldehyde, cyclopropyl-methoxy-acetaldehyde, cyclopropoxyacetaldehyde, 2-methoxy-ethoxy-acetaldehyde, 2-ethoxyethoxy-acetaldehyde, 2-methoxy(1-methyl-ethoxy)-acetaldehyde, 2-ethoxy(1-methyl-ethoxy)-acetaldehyde, phenoxy-acetaldehyde, 2-methoxy-2-methyl-acetaldehyde, 2-ethoxy-2-methyl-acetaldehyde, 2-n-propoxy-2-methyl-acetaldehyde, 2-(i-propoxy)-2-methyl-acetaldehyde, 2-(n-butoxy)-2-methyl-acetaldehyde, 2-(i-butoxy)-2-methyl-acetaldehyde, 2-(tert.-butoxy)-2-methylacetaldehyde, 2-cyclopropylmethoxy-2-methyl-acetaldehyde, 2-cyclopropoxy-2-methyl-acetaldehyde, 2-methoxy-ethoxy-α-methyl-acetaldehyde, 2-ethoxy-ethoxy-α-methyl-acetaldehyde, 2-methoxy(1-methyl-ethoxy)α-methyl-acetaldehyde, 2-methoxy-2,2-dimethylacetaldehyde, 2-ethoxy-2,2-dimethyl-acetaldehyde, 2-cyclopropylmethoxy-acetaldehyde, 2-ω-butoxy-2,2-dimethyl-acetaldehyde, methylthio-acetaldehyde, ethylthio-acetaldehyde, n-propylthio-acetaldehyde, i-propylthio-acetaldehyde, cyclopropyl-methylthio-acetaldehyde, 3-methoxy-propanal, 3-ethoxypropanal, 3-n- and 3-i-propoxy-propanal, 3-n-, 3-i- and 3-tert.-butoxy-propanal, 3-cyclopropoxy-propanal, 3-cyclopropylmethoxy-propanal, 3-methoxy-3-methyl-propanal, 3-ethoxy-3-methyl-propanal, 3-n- and 3-i-propoxy-3-methyl-propanal, 3-n-, 3-i- and 3-tert.-butoxy-3-methyl-propanal, 2-, 3- and 4-methoxybutanal, 2-, 3- and 4-ethoxy-butanal, 2-methylthio-propanal, 2-ethylthiopropanal, 3-methylthio-propanal, 3-ethylthiopropanal, 2-methylthio-butanal, 3-methylthio-butanal, 4-methylthio-butanal, furfural, tetrahydrofurfural, thiophene, 5-bromo-thiophene, 5-methylfurfural and pyrane-carbaldehyde.

If an aldehyde with an optically active centre is used in this process, each enantiomeric form can be employed separately, or the racemate can also be employed. In carrying out the process, it may be advantageous, in the case of aldehydes which possess amino groups, to protect these amino groups with suitable protective groups forming, for example, acetamido or phthalimido, and to split off the protective groups again after the reaction. If can also be advantageous to protect hydroxyl groups in the aldehydes, but in general this is not necessary.

Conveniently the aldehyde may be used in the form of an acetal or hemi-acetal which can be converted into the aldehyde with an acid in situ, the reaction medium being then adjusted, if required, to the desired pH value with the 4,6-di-(aminoglycosyl)-1,3-diaminocyclitol (for example sisomycin) as a base and/or also additionally using an inorganic or organic base.

A preferred process for preparing predominantly derivatives which have a said substituent of the formula V on only one nitrogen atom is carried out by preparing a solution of a 4,6-di-(aminoglycosyl)-1,3-diaminocyclitol (for example sisomycin) in a protic solvent, adjusting the pH to the desired value as described above, appropriately by means of an acid or base, adding at least one equivalent, and preferably an excess, of the aldehyde (for example furfural, methoxyacetaldehyde, ethoxyacetaldehyde or 3-methoxypropanal) and shortly thereafter (for example after from 5 to 15 minutes) adding about one molar equivalent of the reducing agent, preferably a borohydride, such as, for example, dimethylaminoborane or sodium cyanoborohydride. The reaction has frequently ended after 30 minutes. However, it can also be advantageous to warm the solution to an elevated temperature for some time in order to obtain, as described above, a better yield of the desired compound.

The end of the reaction can be determined, for example, by carrying out a thin layer chromatography test on a sample of the reaction medium.

The desired components can be separated and isolated by standard methods, as described above, preferably by chromatography on gels or ion exchangers. If in the preferred process the derivatives of the 4,6-di-(aminoglycosyl)-1,3-diaminocyclitols to be obtained are those which are polysubstituted on the nitrogens, the procedure is as described above, but, for example, according to Example 10 with more aldehyde and reducing agent being added, corresponding to the desired degree of substitution. Thus, for derivatives which are substituted on two nitrogen atoms by the substituent of the formula V, two equivalents, and preferably a larger excess, of the aldehyde (for example furfural, methoxyacetaldehyde ethoxyacetaldehyde or 3-methoxypropanal) are added, and shortly thereafter (5 to 15 minutes) about two molar equivalents of the reducing agent are added. It is also possible to use as starting compounds 4,6-di-(aminoglycosyl)-1,3-diaminocyclitols which are protected on one or more nitrogen atoms by suitable protecting groups and which, after introducing the substituent of the formula V and removing the protective group by standard methods, yield the desired derivatives.

4,6-Di-(aminoglycosyl)-1,3-diaminocyclitols with a protective group on the two reactive amino groups in the 6'-position and 1-position (for example 6'-N-butoxycarbonylsisomycin and 1-N-butoxycarbonyl-sisomicin) are preferred for this purpose and are easily accessible. After removing the protective group(s), good yields of mono-derivatives of the 4,6-di-(aminoglycosyl)-1,3-diaminocyclitols, which are not substituted by said substituent of formula V on either of the nitrogen atoms in positions 1 and 6'. The 1,6'-di-N-protected derivatives (for example 1,6'-di-N-butoxycarbonylsisomicin) are also suitable for the preparation of the derivatives described above.

The starting compounds containing amino-protective groups can be prepared by methods which are in themselves known.

The expression "protective group" refers to groups which protect the amino groups from chemical reactions and which can be easily removed again after the reaction has been completed. Examples of amino-protective groups are benzyl, 4-nitrobenzyl, triphenylmethyl and 2,4-dinitrophenyl; acyl groups such as acetyl, propionyl and benzoyl; alkoxycarbonyl groups, such as methoxycarbonyl, ethoxycarbonyl, 2,2,2-trichloroethoxycarbonyl, t-butoxycarbonyl and 2-iodoethoxycarbonyl; and arylalkoxycarbonyl groups, such as carbobenzyloxy and 4-methoxybenzyloxycarbonyl groups.

When introducing the amino-protective groups, these are usually added in the form of the acid imidazole derivatives the acid azide or an active ester, such as ethylthiol trifluoroacetate, N-benzyloxycarbonyloxysuccinimide or p-nitrophenyl trichloroethyl carbonate. The protective group thus originates from a compound of the formula A-B, wherein A becomes the protective group, such as, for example, the acid part of an active ester, and B represents a group which is easily split off during the reaction (for example imidazoline).

In process variant (c) described above a Schiff's base is first prepared and this is then reduced. In this process variant the —NH₂ amino group being substituted is first converted to a group of the formula

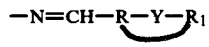

wherein R, Y and R₁ have the same meaning as defined hereinbefore. This is then reduced, and if appropriate the protective groups are removed, the desired derivative being isolated as such or after conversion into a pharmaceutically acceptable acid addition salt.

In process variant (e) reduction may be effected with an amide-reducing agent containing hydrogen.

The process is usually carried out in an inert organic solvent in which the starting compounds and the reducing agent are soluble, and it can be advantageous for any protective groups to be chosen so that they advantageously modify the solubility of the starting compound in the inert organic solvent.

Examples of particularly suitable solvents are ether, dioxane, tetrahydrofurane, diethylene glycol dimethyl ether and the like.

Preferred reducing agents are aluminium hydrides and borohydrides, such as lithium aluminium hydride, lithium trimethoxyaluminium hydride, aluminium hydride, diborane, di-isoamylborane and 9-borabicyclo[3.3.1.]nonane.

In general, diborane is preferably used as the reducing agent, but if the starting compound possesses a double bond, such as in the case of the N-acylsisomicins, N-acylverdamycins and N-acyl-antibiotic 66-40 B, N-acyl-antibiotic 66-40 D and N-acyl-antibiotic G-52 derivatives, lithium aluminium hydride is preferably used.

If the acyl side chain in the substituted 4,6-di(aminoglycosyl)-1,3-diaminocyclitol has an optically active centre, each stereoisomer can be employed individually for the reduction, or a mixture thereof can be employed, and the corresponding diastereoisomer, or a mixture thereof, is obtained.

In the case of process variant (a) a suitable carbodiimide, is for example, dicyclohexylcarbodiimide. In general it is preferable to use a reactive derivatives of said acid of general formula VII as an acylating agent. Examples of reactive derivatives of the acid include esters, azides, imidazole derivatives, anhydrides and chlorides.

The pH which is favourable for the reaction may be determined by evaluation of reaction medium samples, for example, in a thin layer chromatogram.

In order to prepare derivatives substituted on several nitrogen atoms, several equivalents of the acylating agent are desirably added, according to the desired degree of substitution.

In the case of process variant (d) the amino groups of the 4,6-di-(amino-glycosyl)-1,3-diaminocyclitols can be free or activated. One example of an activating group is trifluoromethylsulphonyl.

If compounds which are substituted on several nitrogen atoms are to be prepared by this process, several equivalents of the alkylating agent are desirably added, according to the desired degree of substitution.

The following examples illustrate the invention further.

For the avoidance of doubt, it should be noted that any references herein to sysomycin should be construed as referring to sysomicin.

EXAMPLE 1 A

1-N-[2-(2-Ethoxy-ethoxy)]ethylsisomycin, 3''-N-[2-(2-ethoxy-ethoxy)]ethylsisomycin, 3-N-[2-(2-ethoxy-ethoxy)]-ethylsisomycin and 2'-N-[2-(2-ethoxy-ethoxy)-]ethylsisomycin.

50 ml of water and 1 ml of 96% strength sulphuric acid are added to 3 g of 2-(2-ethoxy-ethoxy) acetaldehyde dimethyl acetal, dissolved in 50 ml of methanol. The mixture is warmed briefly to the reflux temperature (5 minutes) and cooled with an ice bath and 3.35 g of sisomycin base, dissolved in 80 ml of water/methanol (5:3) are added. If necessary, the pH is adjusted to 5 using a little more sisomycin base. The solution is stirred for 30 minutes at room temperature, 470 mg of sodium cyanoborohydride are added and the mixture is stirred for a further 30 minutes at room temperature. In order to bring the reaction to completion, the mixture is then warmed to the reflux temperature for 30 minutes and thereafter the reaction solution is evaporated to dryness in vacuo.

The evaporation residue contains the desired compounds of the example in the form of their sulphuric acid addition salts. The residue is dissolved in a mixture of methanol and 25% strength aqueous ammonium hydroxide solution, the salt precipitate which has thereby separated out is filtered off and the filtrate is evaporated to dryness in vacuo. This operation is repeated until the residue can be dissolved in about 20 ml of methanol to give a clear solution.

The compounds of this example are separated by chromatography on 225 g of silica gel, the column first being eluted with a chloroform/methanol (3:1) mixture and then with a mixture of chloroform/methanol/25% strength aqueous ammonium hydroxide (15:5:1). The eluate is collected in fractions of 10 ml, and the pure fractions found to be identical in the thin layer chromatogram are combined. The first fraction gives 0.21 g of 1-N[2-(2-ethoxy-ethoxy)]ethylsisomycin, the second fraction gives 82 mg of 3″-N-[2-(2-ethoxy-ethoxy)] ethylsisomycin, the third fraction gave 82 mg of 3-N-[2-(2-ethoxy-ethoxy)] ethylsisomycin and 195 mg of 2′-N[2-(2-ethoxyethoxy)]ethylsisomycin are obtained from fraction 4. Tables 1, 2, 3 and 4 give the characteristics of the compounds.

1 B.

Instead of sulphuric acid, another acid, such as, for example, acetic acid, trifluoroacetic acid, p-toluenesulphonic acid, hydrochloric acid or phosphoric acid, can also be quite successfully used for the saponification of the acetal according to Example 1 A.

1 C.

Comparable yields are obtained in the procedure according to Example 1 A if sodium cyanoborohydride is replaced by another reducing agent of the hydride donor type, such as, for example, sodium borohydride, dimethylaminoborane, morpholinoborane or tetrabutylammoniumcyanoborohydride.

1 D.

Any other organic or inorganic base can be successfully used for dissolving the evaporation residue in the procedure according to Example 1 A. Comparable yields were obtained, for example, with the bases mentioned by way of example in Example 2 C.

1 E.

Instead of methanol, other solvents can also be used in a procedure analogous to Example 1 A. Favourable results are obtained, for example, with ethanol, dimethylformamide, dimethylsulphoxide and glycol monomethyl ether.

EXAMPLE 2A

6′-N-(2-Ethoxy-ethyl)-sisomycin 1.3 ml of concentrated sulphuric acid in 50 ml of water were added to 3.24 g of 2-ethoxy-acetaldehyde diethyl acetal, dissolved in 50 ml of methanol, and the mixture was briefly heated to the reflux (5 minutes). The solution is cooled with an ice bath and neutralised with triethylamine, and 4.5 g of sisomycin base are added. The mixture is first stirred at room temperature for 30 minutes, 0.63 g of sodium cyanoborohydride is added and the mixture is left at room temperature for a further 30 minutes.

The mixture is evaporated to dryness in vacuo and a residue is obtained which contains 6′-N-(2-ethoxy-ethyl)sisomycin. The compound is purified by chromatography on 225 g of silica gel, the column having been eluted analogously to Example 1A.

Table 5 gives the characteristics determined for 6′-N-(2-ethoxy-ethyl)-sisomycin.

2B.

Instead of sulphuric acid, another acid, such as, for example, acetic acid, trifluoroacetic acid, p-toluenesulphonic acid, hydrochloric acid, phosphoric acid or nitric acid, can also be used for the saponification of the acetal according to Example 2A, and this does not substantially adversely affect the course of the reaction.

2C.

For the neutralisation, any other inorganic or organic base, such as, for example, alkali metal hydroxides and alkaline earth metal hydroxides, carbonates or bicarbonates, ammonia, primary, secondary and tertiary aliphatic and aromatic amines or heterocyclic bases, can be used in a procedure analogous to Example 2A. A basic ion exchanger can also be used successfully. Comparable yields are obtained, for example, using sodium hydroxide, potassium hydroxide and calcium hydroxide, calcium oxide, sodium carbonate and potassium carbonate, sodium bicarbonate and potassium bicarbonate, ethylamine, methyl-ethylamine, triethylamine, hydroxyethylamine, aniline, pyridine and piperidine.

2D.

Comparable yields are obtained in the procedure according to Example 2A if sodium cyanoborohydride is replaced by another reducing agent according to Example 1C.

EXAMPLE 3A

1-N-(2,2-Dimethyl-2-methoxy-ethyl)-sisomycin 11.2 g of 2,2-dimethyl-2-methoxy-acetaldehyde in 150 ml of methanol are added to 50 g of sisomycin sulphate, dissolved in 1.5 liters of water/methanol (3:2). After stirring the mixture at room temperature for 30 minutes, 4.6 g of sodium cyanoborohydride are added and the mixture is stirred at room temperature for 30 minutes and warmed to the reflux temperature for 45 minutes. It is evaporated to about 50 ml in vacuo, the pH is adjusted to 9 with 25 percent strength aqueous ammonium hydroxide, and 200 ml of methanol are added. The precipitate which has separated out is filtered off and the filtrate is evaporated to dryness in vacuo, after which the compounds according to the invention are in the evaporation residue.

The compounds are separated by chromatography on a column of 1 kg of silica gel. For this, the column is first eluted with a chloroform/methanol mixture (4:1) and then with chloroform/methanol/25 percent strength aqueous ammonium hydroxide (15:10:2). The fractions determined as being identical by thin layer chromatography are combined. This gave 5.4 g of 1-N-(2,2-dimethyl-2-methoxy-ethyl)-sisomycin. Table 1 gives the characteristics of the compound.

3B.

Instead of sisomycin sulphate, any other acid addition salt of sisomycin base, such as, for example, the acid addition salt with acetic acid, trifluoroacetic acid, p-toluenesulphonic acid, hydrochloric acid, phosphoric acid or nitric acid, can also be advantageously used.

3C.

For the use of other reducing agents, the statement made in Example 1C applies analogously to Example 3A.

EXAMPLE 4A

1-N(2-Methoxy-ethyl)-sisomycin, 3-N(2-methoxy-ethyl)-sisomycin, 3''-N(2-methoxy-ethyl)-sisomycin and 2'-N(2-methoxyethyl)-sisomycin.

A solution of 50 g of sisomycin sulphate, in 1.5 liters of water/methanol (3:2) is adjusted to a pH value of 7 with triethylamine, 5.3 g of methoxyacetaldehyde are added and the mixture is stirred at room temperature for 30 minutes. Thereafter, 4.6 g of sodium cyanoborohydride are added and the mixture is stirred at room temperature for 30 minutes and at the reflux temperature for 45 minutes. It is evaporated to about 50 ml in vacuo, the pH is adjusted to 9 with 25 percent strength aqueous ammonium hydroxide, 200 ml of methanol are added and the precipitate which has separated out is filtered off. The filtrate is evaporated to dryness in vacuo. The evaporation residue contains the compounds of this example.

The compounds are separated by chromatography on a column of 1 kg of silica gel. The column is first eluted with methanol and then with chloroform/methanol/25 percent strength aqueous ammonium hydroxide (5:5:1), and fractions found to be identical by thin layer chromatography are combined. 5.4 g of 1-N(2-methoxy-ethyl)-sisomycin were obtained from fraction 1, 0.3 g of 3''-N(2-methoxy-ethyl)-sisomycin was obtained from fraction 2, 0.32 g of 3-N(2-methoxy-ethyl)-sisomycin was obtained from fraction 3 and 0.9 g of 2'-N(2-methoxy-ethyl)-sisomycin was obtained from fraction 4. Tables 1, 3, 2 and 4 give the characteristics of the compound.

4B.

For the use of other sisomycin acid addition salts in Example 4, the statement made in Example 3B applies analogously.

4C.

For the use of other reducing agents, the statement made in Example 1C applies analogously.

4D.

For the suitability of other bases for the neutralisation, the statement made under Example 2C applies analogously.

EXAMPLE 5A

1-N[2-(n-Propoxy-ethyl)]-sisomycin, 3-N[2-(n-propoxy-ethyl)]-sisomycin and 2'-N[2-(n-propoxy-ethyl)]sisomycin.

A solution of 6.92 g of sisomycin sulphate in 200 ml of methanol/water (3:2) is adjusted to pH 5 with 2 N sulphuric acid, and 1.02 g of n-propoxy-acetaldehyde are added. The mixture is stirred at room temperature for 30 minutes, 0.63 g of sodium cyanoborohydride is added and the mixture is stirred first at room temperature for 30 minutes and than at the reflux temperature for 15 minutes. The cooled solution is neutralised with a basic ion exchange resin (for example Amberlite IRA 410, OH form) and filtered and the filtrate is evaporated to dryness. The evaporation residue contains the compounds, according to the invention, of this example. The compounds are separated by chromatography on a silica gel column of 450 g of silica gel.

Identical fractions are combined and 540 mg of 1-N[2-(n-propoxy)-ethyl]sisomycin, 200 mg of 3-N[2-(n-propoxy)-ethyl]sisomycin and 600 mg of 2'-N[2-(n-propoxy)ethyl]sisomycin are obtained. Tables 1, 2 and 4 give the characteristics determined for the compounds.

5B.

For the use of other acid addition salts of sisomycin, the statement made in Example 3B applies analogously.

5C.

For the use of other reducing agents in the procedure according to Example 5, the statement made in Example 1C applies analogously.

5D.

For the suitability of other bases in the procedure according to Example 5, the statement made in Example 2C applies analogously.

EXAMPLE 6A

1-N-(3-Methoxy-propyl)-sisomycin, 3-N-(3-methoxy-propyl)-sisomycin, 3''-N-(3-methoxy-propyl)-sisomycin and 2'-N-(3-methoxy-propyl)-sisomycin.

1 ml of 96 percent strength sulphuric acid in 50 ml of water is added to a solution of 2.7 g of 3-methoxypropionaldehyde dimethyl acetal in 50 ml of methanol. The mixture is warmed briefly (5 minutes) to the reflux temperature, cooled to room temperature and neutralised with 2 N aqueous sodium hydroxide. 6.92 g of sisomycin sulphate in 200 ml of methanol/water (3,2) are added to this solution, the pH of the solution first being adjusted to 7 by adding aqueous sodium hydroxide, the mixture is stirred at room temperature for 30 minutes, 0.63 g of sodium cyanoborohydride is added and the mixture is stirred at room temperature for a further 30 minutes and then at the reflux temperature for 30 minutes.

The cooled solution is neutralised with aqueous sodium hydroxide and evaporated in vacuo.

The evaporation residue contains the compounds of this example. They are separated by chromatographing the residue by a procedure analogous to that in Example 1. Tables 1, 2, 3 and 4 give the characteristics of the compound.

6B.

For the use of other sisomycin acid addition salts in Example 6, the statement made in Example 3B applies analogously.

6C.

Other reducing agents can be used in Example 6A in a manner analogous to that in Example 1C.

6D.

The procedure in the neutralisation can also be analogous to Example 2C.

EXAMPLE 7

6'-N-(2-Ethoxy-acetyl)-sisomycin 1.87 g of N-(ethoxy-acetyl)-succinimide are added to 4.47 g of sisomycin base in 200 ml of methanol and the mixture is stirred for 24 hours. It is evaporated to dryness in vacuo and a residue is obtained which contains 6'-N-(2-ethoxy-acetyl)-sisomycin. The residue is purified by chromatography over a silica gel column. The compound had the following $R_F$ values: chloroform/methanol/25 percent strength aqueous ammonium hydroxide (15:10:2): 0.54 (fluorescein: 0.34)
2:2:1): 0.79 (fluorescein: 0.60)
(5:5:1): 0.54 (fluorescein: 0.57)

EXAMPLE 8

6'-N(2-Ethoxy-ethyl)-sisomycin

Hexamethyldisilazane is added dropwise to a suspension of 1 g of 6'-N-(2-ethoxy-acetyl)-sisomycin in 200 ml of tetrahydrofurane at room temperature under a nitrogen atmosphere until a clear solution is obtained, and 3 g of lithium aluminium hydride are added. The solution is kept at the reflux temperature for 3 hours, water is added dropwise until no further frothing occurs and the mixture is then adjusted to pH 2 with 0.2 N hydrochloric acid, warmed briefly (5 minutes) to the reflux temperature and neutralised. It is evaporated to dryness in vacuo, after which a residue is obtained which contains 6'-N-(2-ethoxy-ethyl)sisomycin.

The compound was purified on a silica gel column analogously to Example 1A, and Table 5 gives the characteristics.

EXAMPLE 9

Acid addition salts

A. Sulphate salts (sulphuric acid addition salts)

5.0 g of 1-N(2-ethoxy-ethyl)-sisomycin are dissolved in 25 ml of water and the pH value of the solution is adjusted to 4.5 using 1 N sulphuric acid. The solution is then poured into about 300 ml of methanol, whilst stirring vigorously, stirring is continued for about 10 to 20 minutes and the mixture is filtered. The precipitate is washed with methanol and dried at about 60° C. in vacuo, 1-N(2-ethoxy-ethyl)-sisomycin sulphate being obtained. The sulphate salts of the compounds of all the examples can be prepared in the same manner.

B. Hydrochloride salts 5.0 g of 1-N(2-methoxy-ethyl)-sisomycin are dissolved in 25 ml of water. The solution is then acidified to a pH value of 5 with 2 N hydrochloric acid. Lyophilisation gives 1-N(2-methoxy-ethyl)sisomycin hydrochloride.

The hydrochloride salts of all the compounds of the examples can be prepared in a similar manner.

EXAMPLE 10

6'-N(2-Ethoxyacetyl)-sisomycin 1.84 g (0.015 mol) of ethoxy-acetyl chloride were added to 4.5 g (0.01 mol) of sisomycin base in 100 ml of methanol/water (1:1) at room temperature and the mixture was boiled at the reflux temperature for 2 hours and then stirred at room temperature after 16 hours. It was evaporated to dryness in vacuo and the compound of this example was obtained in the evaporation residue. The pure compound was obtained by chromatography of the evaporation residue on a column of 220 g of silica gel, the column being first eluted with 2.5 l of a chloroform/methanol/water.ammonium hydroxide (25%) mixture (20:3:0.5) and thereafter with 3 l of a mixture having the composition 15:5:1. Fractions found to be identical in the thin layer chromatogram were combined, after which 375 mg of 1-N-(2-ethoxyacetyl)-sisoanicin were obtained.

The tables which follow indicate some of the characteristics determined for important compounds of the invention, the compounds being derivatives of sisomycin which are substituted by the radical

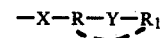

The Rf values were determined together with the comparison dyestuff fluorescin. In system 3, methyl red is additionally indicated in the 2nd position as a comparison dyestuff. The determination was carried out on silica gel finished plates. Silica gel finished plates 60 F 254 from Messrs. Merck Darmstadt, Federal Republic of Germany, Article No. 5715 were used.

The running agents used were:
System 1: chloroform/methanol/25 percent strength aqueous ammonium hydroxide (15:10:2)
System 2: chloroform/methanol/25 percent strength aqueous ammonium hydroxide (5:5:1)
System 3: butanol/acetone/25 percent strength aqueous ammonium hydroxide (5:4:1)

In the case of the mass spectra, only the characteristic peaks were indicated.

The empirical formula and molecular weight were calculated, or were obtained from the mass spectrum.

The tables are based on the sisomycin of the formula II.

The derivatives are compounds in which one hydrogen atom on a nitrogen atom is replaced by the substituent

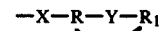

which is indicated in a shortened form as R" in the tables for reasons of better clarity.

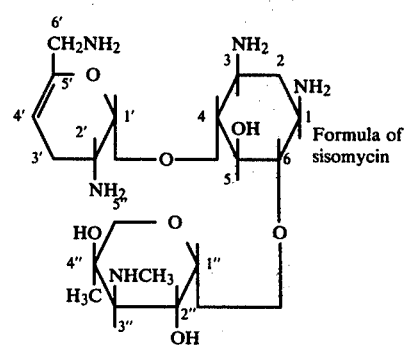

Formula of sisomycin

Table 1

| Serial No. | R" | Empirical formula (molecular weight) | Rf values System 1 | System 2 | System 3 | Mass spectrum |
|---|---|---|---|---|---|---|
| 1 | —$CH_2$—$CH_2$—$OCH_3$ | $C_{22}H_{43}N_5O_8$ (505) | 0.46 (0.34) | 0.48 (0.51) | 0.15 (0.08 0.45) | 505,488,388,362,347 256,249,160,130,118 |
| 2 | —$CH_2$—$CH_2$—$OC_2H_5$ | $C_{23}H_{45}N_5O_8$ (519) | 0.51 (0.34) | 0.53 (0.51) | 0.16 (0.08 0.45) | 519,502,376,361,263, 256,160 |
| 3 | —$CH_2$—$CH_2$—$OC_3H_7(n)$ | $C_{24}H_{47}N_5O_8$ (533) | 0.57 (0.34) | 0.59 (0.51) | 0.25 (0.08 | 533,516,416,390,357, |

Table 1-continued (R″ on N-1)

| Serial No. | R″ | Empirical formula (molecular weight) | Rf values System 1 | Rf values System 2 | Rf values System 3 | Mass spectrum |
|---|---|---|---|---|---|---|
| 4 | —CH$_2$—CH$_2$—OC$_3$H$_7$(i) | C$_{24}$H$_{47}$N$_5$O$_8$ (533) | 0.56 (0.34) | 0.56 (0.51) | 0.28 (0.08 0.42) | 277,256,160, 533,390,277,256,160 |
| 5 | —CH$_2$—CH$_2$—OC$_4$H$_9$(n) | C$_{25}$H$_{49}$N$_5$O$_8$ (547) | 0.58 (0.34) | 0.59 (0.51) | 0.28 (0.08 0.42) | 547,404,389,371,291, 256,160 |
| 6 | —CH$_2$—CH$_2$—OC$_4$H$_9$(i) | C$_{25}$H$_{49}$N$_5$O$_8$ (547) | 0.57 (0.34) | 0.58 (0.51) | 0.20 (0.08 0.45) | 547,430,404,371,291, 256,160,127 |
| 7 | —CH$_2$—CH$_2$—CH$_2$—OCH$_3$ | C$_{23}$H$_{45}$N$_5$O$_8$ (519) | 0.38 (0.29) | 0.43 (0.52) | 0.14 (0.07 0.42) | 519,376,361,263,256, 160 |
| 8 | —CH$_2$—CH$_2$—CH$_2$—S—CH$_3$ | C$_{23}$H$_{45}$N$_5$O$_7$S (535) | 0.42 (0.26) | 0.41 (0.54) | 0.25 (0.08 0.44) | 535,392,377,279,256, 160,127 |
| 9 | —CH$_2$—CH$_2$—CH$_2$—OC$_2$H$_5$ | C$_{24}$H$_{47}$N$_5$O$_8$ (533) | 0.42 (0.29) | 0.47 (0.52) | 0.18 (0.07 0.42) | 534,533,390,375,277 256,160,130 |
| 10 | —CH$_2$—CH$_2$—CH(CH$_3$)—OCH$_3$ | C$_{24}$H$_{47}$N$_5$O$_8$ (533) | 0.40 (0.38) | | | 533,390,277,256,160 127 |
| 11 | —CH$_2$—C(CH$_3$)$_2$—OCH$_3$ | C$_{24}$H$_{47}$N$_5$O$_8$ (533) | 0.36 (0.30) | 0.40 (0.54) | 0.21 (0.08 0.44) | 534,533,516,390,277, 256,160,375,249,118 |
| 12 | —(CH$_2$)$_2$—O—(CH$_2$)$_2$—OCH$_3$ | C$_{24}$H$_{47}$N$_5$O$_9$ (549) | 0.39 (0.29) | 0.46 (0.52) | 0.15 (0.07 0.44) | 550,549,406,293, 256,160,130 |
| 13 | —(CH$_2$)$_2$—O—CH(CH$_3$)—CH$_2$—OCH$_3$ | C$_{25}$H$_{49}$N$_5$O$_9$ (563) | 0.45 (0.29) | 0.52 (0.52) | 0.20 (0.07 0.44) | 563,420,307,256, 160,130 |
| 14 | —(CH$_2$)$_2$—O—(CH$_2$)$_2$—OC$_2$H$_5$ | C$_{25}$H$_{49}$N$_5$O$_9$ (563) | 0.48 (0.29) | 0.58 (0.63) | 0.27 (0.08) 0.41) | 563,446,420,405, 387,307,256,160, 127 |
| 15 | —CH$_2$-(furyl) | C$_{24}$H$_{41}$N$_5$O$_8$ (527) | 0.39 (0.30) | 0.37 (0.54) | 0.20 (0.08 0.44) | 527,510,401,384, 271,160 |
| 16 | —CH$_2$-(5-methylfuryl) | C$_{25}$H$_{43}$N$_5$O$_8$ (541) | 0.43 (0.30) | 0.41 (0.54) | 0.24 (0.08 0.44) | 541,524,285,160, 95, |
| 17 | —CH$_2$-(5-chlorofuryl) | C$_{24}$H$_{40}$ClN$_5$O$_8$ (561) | 0.41 (0.38) | 0.40 (0.54) | 0.23 (0.08 0.44) | 561,435,418,400, 360,318,305,160 |
| 18 | —CH$_2$-(5-bromofuryl) | C$_{24}$H$_{40}$BrN$_5$O$_8$ (606) | 0.40 (0.30) | 0.40 (0.54) | 0.25 (0.08 0.44) | 607,605,590,588, 464,462,351,349, 323,321,161,160, 159 |
| 19 | —CH$_2$-(5-bromothienyl) | C$_{24}$H$_{40}$BrN$_5$O$_7$S (622) | 0.39 (0.26) | 0.38 (0.54) | 0.27 (0.08 0.44) | 623,621,367,365, 177,175,160 |
| 20 | —CH$_2$—CH$_2$—O—C$_6$H$_5$ | C$_{27}$H$_{45}$N$_5$O$_8$ (567) | 0.49 (0.29) | 0.42 (0.63) | 0.31 (0.08 0.41) | 567,550,450,424, 409,391,311,256, 160 |
| 21 | —CH$_2$—CH$_2$—S—CH$_3$ | C$_{22}$H$_{43}$N$_5$O$_7$S (521) | 0.44 (0.29) | 0.59 (0.66) | 0.26 (0.09 0.48) | |
| 22 | —CH$_2$—CH$_2$—S—C$_2$H$_5$ | C$_{23}$H$_{45}$N$_5$O$_7$S (535) | 0.52 (0.29) | 0.66 (0.66) | 0.35 (0.09 0.48) | |
| 23 | —C(=O)—CH$_2$OCH$_3$ | C$_{22}$H$_{41}$N$_5$O$_9$ (519) | 0.35 (0.28) | 0.46 (0.63) | 0.23 (0.09 0.45) | |
| 24 | —C(=O)—CH$_2$—OC$_3$H$_7$(n) | C$_{24}$H$_{45}$N$_5$O$_9$ (537) | 0.28 (0.22) | 0.42 (0.51) | 0.09 (0.06 0.33) | |
| 25 | —C(=O)—CH$_2$—OC$_3$H$_7$(i) | C$_{24}$H$_{45}$N$_5$O$_9$ (547) | 0.32 (0.22) | 0.41 (0.48) | 0.15 (0.09 0.41) | |
| 26 | —C(=O)—CH$_2$—OC$_4$H$_9$(n) | C$_{25}$H$_{47}$N$_5$O$_9$ (561) | 0.36 (0.22) | 0.47 (0.48) | 0.18 (0.09 0.41) | |
| 27 | —C(=O)—CH$_2$—OC$_4$H$_9$(i) | C$_{25}$H$_{47}$N$_5$O$_9$ (561) | 0.47 (0.20) | 0.60 (0.46) | 0.38 (0.08 0.38) | |
| 28 | —C(=O)—CH$_2$—S—CH$_3$ | C$_{22}$H$_{41}$N$_5$O$_8$S (535) | 0.23 (0.22) | 0.41 (0.51) | 0.12 (0.06 0.33) | |

Table 1-continued (R″ on N-1)

| Serial No. | R″ | Empirical formula (molecular weight) | Rf values System 1 | System 2 | System 3 | Mass spectrum |
|---|---|---|---|---|---|---|
| 29 | $-(CH_2)_3-S-CH_3$ | $C_{23}H_{45}N_5O_7S$ (535) | 0.42 (0.26) | | | |

Rf values in brackets: (fluorescein, methyl red)

Table 2

(R″ on N-3)

| Serial No. | R″ | Empirical formula (molecular weight) | Rf values System 1 | System 2 | System 3 | Mass spectrum |
|---|---|---|---|---|---|---|
| 1 | $-CH_2-CH_2-OC_2H_5$ | $C_{23}H_{45}N_5O_8$ (519) | 0.45 (0.34) | 0.48 (0.51) | 0.19 (0.08 0.45) | 519, 376, 334, 263 235, 160 |
| 2 | $-CH_2-CH_2-OC_4H_9(n)$ | $C_{25}H_{49}N_5O_8$ (547) | 0.49 (0.34) | 0.51 (0.51) | 0.13 (0.08 0.42) | 547, 530, 404, 291, 160 |
| 3 | $-CH_2-CH_2-OC_3H_7(i)$ | $C_{24}H_{47}N_5O_8$ (533) | 0.48 (0.34) | 0.49 (0.51) | 0.11 (0.08 0.42) | 533, 516, 390, 277, 160 |
| 4 | $-CH_2-CH_2-OC_4H_9(i)$ | $C_{25}H_{49}N_5O_8$ (547) | 0.48 (0.34) | 0.51 (0.51) | 0.11 (0.08 0.45) | 547, 530, 404, 291 263, 230, 160, |
| 5 | $-(CH_2)_2-O-(CH_2)_2-OCH_3$ | $C_{24}H_{47}N_5O_9$ (549) | 0.29 (0.29) | 0.34 (0.52) | 0.10 (0.07 0.44) | 550, 549, 358, 293, 265, 232, 160 |
| 6 | $-(CH_2)_2-O-(CH_2)_2-OC_2H_5$ | $C_{25}H_{49}N_5O_9$ (563) | 0.35 (0.29) | 0.44 (0.63) | 0.12 (0.08 0.41) | 563, 420, 372, 307 289, 279, 160 |
| 7 | $-(CH_2)_2-O-\overset{CH_3}{\underset{}{C}H}-CH_2-OCH_3$ | $C_{25}H_{49}N_5O_9$ (563) | 0.39 (0.29) | 0.46 (0.52) | 0.10 (0.07 0.44) | 563, 546, 372, 307, 160 |
| 8 | $-CH_2-CH_2-CH_2-OCH_3$ | $C_{23}H_{45}N_5O_8$ (519) | 0.31 (0.29) | 0.35 (0.52) | 0.09 (0.07 0.42) | 519, 502, 263, 235, 160 |
| 9 | $-CH_2-CH_2-OCH_3$ | $C_{21}H_{43}N_5O_8$ (505) | 0.27 (0.28) | 0.39 (0.56) | 0.12 (0.05 0.37) | 505, 488, 473, 362, 314, 289, 249, 160, 130, 127, 118 |
| 10 | $-CH_2-\overset{CH_3}{\underset{CH_3}{C}}-OCH_3$ | $C_{24}H_{47}N_5O_8$ (533) | 0.25 (0.28) | 0.39 (0.56) | 0.13 (0.05 0.37) | 533, 390, 277, 160, 130, 118 |
| 11 | $-CH_2-CH_2-S-CH_3$ | $C_{22}H_{43}N_5O_7S$ (521) | 0.33 (0.29) | 0.44 (0.66) | 0.17 (0.09 0.48) | |
| 12 | $-CH_2-CH_2-S-C_2H_5$ | $C_{23}H_{45}N_5O_7S$ (535) | 0.36 (0.29) | 0.49 (0.66) | 0.20 (0.09 0.48) | |
| 13 | $-\underset{\underset{O}{\parallel}}{C}-CH_2-O-CH_3$ | $C_{22}H_{41}N_5O_9$ (519) | 0.27 (0.28) | 0.44 (0.63) | 0.19 (0.09 0.45) | |

Rf values in brackets (fluorescein, methyl red)

Table 3

(R″ on N-3″)

| Serial No. | R″ | Empirical formula (molecular weight) | Rf values System 1 | System 2 | System 3 | Mass spectrum |
|---|---|---|---|---|---|---|
| 1 | $-CH_2-CH_2-OC_3H_7(i)$ | $C_{24}H_{47}N_5O_8$ (533) | 0.48 (0.34) | 0.49 (0.51) | 0.27 (0.08 0.42) | 533, 516, 390, 375, 334, 246, 191 |
| 2 | $-CH_2-CH_2-OC_4H_9(i)$ | $C_{25}H_{49}N_5O_8$ (547) | 0.48 (0.34) | 0.51 (0.51) | 0.24 (0.08 0.45) | 547, 530, 404, 334, 260, 191 |
| 3 | $-CH_2-CH_2-OC_4H_9(n)$ | $C_{25}H_{49}N_5O_8$ (547) | 0.49 (0.34) | 0.51 (0.51) | 0.34 (0.08 0.42) | 547, 530, 404, 334, 260, 191 |
| 4 | $-(CH_2)_2-O-(CH_2)_2-OCH_3$ | $C_{24}H_{47}N_5O_9$ (549) | 0.31 (0.29) | 0.39 (0.52) | 0.21 (0.07 0.44) | 549, 532, 406, 334, 262, 191 |
| 5 | $-(CH_2)_2-O-(CH_2)_2-OC_2H_5$ | $C_{25}H_{49}N_5O_9$ (563) | 0.38 (0.29) | 0.48 (0.63) | 0.29 (0.08 0.41) | 563, 546, 420, 334, 276, 191 |
| 6 | $-(CH_2)_2-O-\overset{CH_3}{\underset{}{C}H}-CH_2-OCH_3$ | $C_{25}H_{49}N_5O_9$ (563) | 0.32 (0.29) | 0.39 (0.52) | 0.23 (0.07 0.44) | 563, 388, 276, 191 |
| 7 | $-CH_2-CH_2-O-C_6H_5$ | $C_{27}H_{45}N_5O_8$ (567) | 0.38 (0.29) | 0.31 (0.63) | 0.31 (0.08 0.41) | 567, 550, 424, 334, 280, 191 |
| 8 | $-CH_2-CH_2-CH_2-OCH_3$ | $C_{23}H_{45}N_5O_8$ (519) | 0.31 (0.29) | 0.35 (0.52) | 0.19 (0.07 0.42) | 519, 502, 232, 191, 163 |
| 9 | $-CH_2-CH_2-OCH_3$ | $C_{21}H_{43}N_5O_8$ (505) | 0.37 (0.28) | 0.50 (0.56) | 0.19 (0.05 0.37) | 505, 488, 473, 362, 256, 218, 191, 163, 127 |

Table 3-continued

(R″ on N-3″)

| Serial No. | R″ | Empirical formula (molecular weight) | Rf values System 1 | System 2 | System 3 | Mass spectrum |
|---|---|---|---|---|---|---|
| 10 | —CH$_2$—C(CH$_3$)$_2$—OCH$_3$ | C$_{24}$H$_{47}$N$_5$O$_8$ (533) | 0.31 (0.28) | 0.45 (0.56) | 0.14 (0.05 0.37) | |
| 11 | —CH$_2$—CH$_2$—S—CH$_3$ | C$_{22}$H$_{43}$N$_5$O$_7$S (521) | 0.33 (0.29) | 0.47 (0.66) | 0.35 (0.09 0.48) | |

Rf values in brackets: (fluorescein, methyl red)

Table 4

(R″ on N-2′)

| Serial No. | R″ | Empirical formula (molecular weight) | Rf Values System 1 | System 2 | System 3 | Mass spectrum |
|---|---|---|---|---|---|---|
| 1 | —CH$_2$—CH$_2$—OC$_3$H$_7$(n) | C$_{24}$H$_{47}$N$_5$O$_8$ (533) | 0.39 (0.34) | 0.38 (0.51) | 0.11 (0.08 0.42) | 534, 533, 448, 304, 213, 191,160 |
| 2 | —CH$_2$—CH$_2$—OC$_3$H$_7$(i) | C$_{24}$H$_{47}$N$_5$O$_8$ (533) | 0.37 (0.34) | 0.37 (0.51) | 0.15 (0.08 0.42) | |
| 3 | —CH$_2$—CH$_2$—O—C$_4$H$_9$(n) | C$_{25}$H$_{49}$N$_5$O$_8$ (547) | 0.39 (0.34) | 0.40 (0.51) | 0.12 (0.08 0.42) | 548, 547, 462, 430, 304, 227, 191, 160 |
| 4 | —(CH$_2$)$_2$—O—(CH$_2$)$_2$—OCH$_3$ | C$_{24}$H$_{47}$N$_5$O$_9$ (549) | 0.25 (0.29) | 0.29 (0.52) | 0.08 (0.07 0.44) | 549, 464, 304, 229 191, 160 |
| 5 | —(CH$_2$)$_2$—O—(CH$_2$)$_2$—OC$_2$H$_5$ | C$_{25}$H$_{49}$N$_5$O$_9$ (563) | 0.22 (0.29) | 0.33 (0.63) | 0.15 (0.08 0.41) | 563, 478, 372, 304, 243, 191, 160 |
| 6 | —(CH$_2$)$_2$—O—CH(CH$_3$)—CH$_2$—OCH$_3$ | C$_{25}$H$_{49}$N$_5$O$_9$ (563) | 0.22 (0.29) | 0.27 (0.52) | 0.09 (0.07 0.44) | 563, 478, 387, 372, 304, 243, 191, 160 |
| 7 | —CH$_2$—CH$_2$—O—C$_6$H$_5$ | C$_{27}$H$_{45}$N$_5$O$_8$ (567) | 0.27 (0.29) | 0.22 (0.63) | 0.15 (0.08 0.44) | 568, 567, 482, 304 247, 191, 160 |
| 8 | —CH$_2$—CH$_2$—CH$_2$—OCH$_3$ | C$_{23}$H$_{45}$N$_5$O$_8$ (519) | 0.20 (0.29) | 0.24 (0.52) | 0.12 (0.07 0.42) | 519, 434, 328, 304 199, 191, 160 |
| 9 | —CH$_2$—CH$_2$—O—CH$_3$ | C$_{21}$H$_{43}$N$_5$O$_8$ (505) | 0.20 (0.28) | 0.31 (0.56) | 0.12 (0.05 0.37) | 505, 488, 473, 420 347, 304, 191, 185, 160, 130, 118 |
| 10 | —CH$_2$—C(CH$_3$)$_2$—O—CH$_3$ | C$_{24}$H$_{47}$N$_5$O$_8$ (533) | 0.18 (0.28) | 0.28 (0.56) | 0.12 (0.05 0.37) | 533, 448, 304, 213, 191, 160, 130, 118 |
| 11 | —CH$_2$—CH$_2$—S—CH$_3$ | C$_{22}$H$_{43}$N$_5$O$_7$S (521) | 0.27 (0.29) | 0.35 (0.66) | 0.17 (0.09 0.48) | |
| 12 | —CH$_2$—CH$_2$—S—C$_2$H$_5$ | C$_{23}$H$_{45}$N$_5$O$_7$S (535) | 0.24 (0.29) | 0.32 (0.66) | 0.18 (0.09 0.48) | |

Rf values in brackets: (fluorescein, methyl red)

Table 5

(R″ on N-6′)

| Serial No. | R″ | Empirical formula (molecular weight) | Rf values System 1 | System 2 | System 3 | Mass spectrum |
|---|---|---|---|---|---|---|
| 1 | —CH$_2$—CH$_2$—OC$_2$H$_5$ | C$_{23}$H$_{45}$N$_5$O$_8$ (519) | 0.34 (0.34) | 0.34 (0.51) | 0.11 (0.08 0.45) | 519, 328, 304, 199, 191, 160 |
| 2 | —CH$_2$—CH$_2$—OC$_3$H$_7$(i) | C$_{24}$H$_{47}$N$_5$O$_8$ (533) | 0.37 (0.34) | 0.37 (0.51) | 0.15 (0.08 0.42) | |
| 3 | —CH$_2$—CH$_2$—OC$_4$H$_9$(i) | C$_{25}$H$_{49}$N$_5$O$_8$ (547) | 0.40 (0.34) | 0.40 (0.51) | 0.08 (0.08 0.45) | 547, 304, 227, 191, 160 |
| 4 | —C(=O)—CH$_2$—OC$_2$H$_5$ | C$_{23}$H$_{43}$N$_5$O$_9$ (533) | 0.43 (0.28) | 0.60 (0.63) | 0.31 (0.09 0.45) | |

Rf values in brackets: (fluorescein, methyl red)

The compounds of the invention are antibacterial agents having a broad spectrum of activity and are active against many organisms, especially Gram-negative bacteria, which are resistant towards the corresponding N-unsubstituted antibiotics. The compounds of the invention can be used alone or in combination with other antibiotics in order to prevent the growth of bacteria or to reduce their number. The compounds can be used, for example, for disinfecting laboratory apparatuses or items of dental or medical equipment which are contaminated by Staphylococcus aureus or other bacteria.

Because of the activity of the compounds of the invention against Gram-negative bacteria, they appear particularly useful in combating infections which are caused by Gram-negative organisms, for example species of Proteus and Pseudomonas.

The N-substituted derivatives of the 4,6-di-(aminoglycosyl)-1,3-diaminocyclitols, for example 1-H(2-ethoxyethyl)-sisomicin can also be employed in veterinary medicine, especially in the treatment of mastitis in cattle and of diarrhoea, caused by Salmonellae, in pets, such as dogs and cats.

In general, the dose to be administered of the compounds of the invention depends on the age and weight of the subject being treated, on the nature of the administration and on the type of severity of the bacterial infection. The dosage of the derivatives of the 4,6-di-(aminoglycosyl)-1,3-diaminocyclitols is usually similar to the dosage of the corresponding N-unsubstituted antibiotics.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils for example ground nut oil, glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters). microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of these mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from 100 mg to 3 g of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above mentioned diseases in warm-blooded animals, which comprises administering to the animals a compound of the invention alone or in admixture with a diluent or in the form of a medicament according to the invention.

These active compounds will be administered perorally, parenterally (for example intramuscularly, intraperitoneally or intravenously), rectally or topically, preferably orally, topically or intramuscularly. Preferred pharmaceutical compositions and medicaments are therefore those adapted for oral, parenteral and topical administration, such as tablets, injection solutions and ointments, creams and lotions, respectively. Administration in the method of the invention is preferably orally, parenterally or topically.

In general it has proved advantageous to administer parenterally amounts of from about 1 mg to 15 mg/kg of body weight from 2 to 4 times per day, to achieve effective results. Preferred topical formulations are those containing from about 0.1 to 3.0 g of the active compounds per 100 g of the formulation. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above mentioned minimum dosage rate, whilst other cases the upper limit mentioned must be exceeded to achieve the desired results. Where larger amounts are administered it can be advisable to divide these into several individual administrations over the course of the day.

The examples which follow illustrate pharmaceutical compositions:

| Tablet | Formulation 1 | | |
|---|---|---|---|
| | 10 mg tablet | 25 mg tablet | 100 mg tablet |
| 1-N[2-(n-propoxy)-ethyl]-sisomicin | 10.50+ mg | 26.25+ mg | 105.00+ mg |
| lactose | 197.50 mg | 171.25 mg | 126.00 mg |
| maize starch | 25.00 mg | 25.00 mg | 35.00 mg |
| polyvinylpyrrolidone | 7.50 mg | 7.50 mg | 7.50 mg |
| magnesium stearate | 2.50 mg | 2.50 mg | 3.50 mg |
| + 5% excess | | | |

Preparation

A suspension of 1-N-[2-(n-propoxy)-ethyl]sisomicin, lactose and polyvinylpyrrolidone is prepared and this is spray-dried. The maize starch and magnesium stearate are added, the components are mixed and the mixture is pressed to form tablets.

| Ointment | Formulation 2 |
|---|---|
| 1-N(2-methoxy-ethyl)-sisomicin | 1.0 g |
| methylparaben U.S.P. | 0.5 g |
| propylparaben U.S.P. | 0.1 g |
| petrolatum | to 1,000 g |

Preparation (1) The petrolatum is melted;
(2) 1-N(2-methoxy-ethyl)-sisomicin, methylparaben and propylparaben are mixed with about 10% of the molten petrolatum;
(3) The mixture is put into a colloid mill; and
(4) The remainder of the petrolatum is added, whilst stirring, and the mixture is cooled until it is semi-solid. The product is filled into suitable containers.

| Injection solution | Formulation 3 | |
|---|---|---|
| | per 2.0 ml phial | per 50 liters |
| 1-N(2-ethoxy-ethyl)-sisomicin sulphate | 84.0 mg+ | 2,100.0 grams |
| methylparaben, U.S.P. | 3.6 mg | 90.0 grams |
| propylparaben, U.S.P. | 0.4 mg | 10.0 grams |
| sodium bisulphite, U.S.P. | 6.4 mg | 160.0 grams |
| disodium ethylenediaminetetraacetate dihydrate | 0.2 mg | 5.0 grams |
| water, U.S.P. q.s. | 2.0 mg | 50.0 liters |
| + 5% excess | | |

Preparation of a 50 liter batch

Approximately 35 liters of water for injection purposes are put into a suitable vessel of stainless steel and heated to about 70° C. The methylparaben and propylparaben are added to the hot water and dissolved, whilst stirring. After dissolving, the solution is cooled to about 25°–30° C. and flushed with nitrogen for at least 10 minutes. The following operations are carried out under nitrogen. The disodium EDTA is added to the solution, with sodium bisulphite, and thereafter the 1-N(2-ethoxy-ethyl)sisomicin sulphate is added and dissolved. The volume of the solution is made up to 50 liters and the solution stirred until it is homogeneous.

The solution is filtered under sterile conditions using a filter which retains bacteria, and the filtrate is collected in a tank.

The filtrate is filled and sealed aseptically into sterile, pyrogen-free phials.

What is claimed is:

1. A compound of the formula

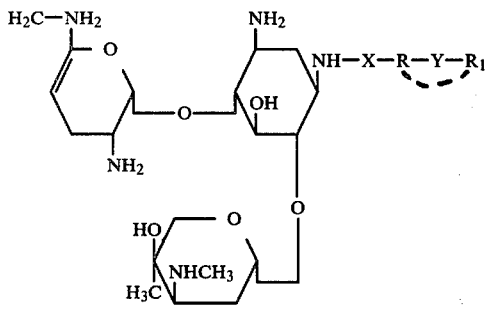

or a pharmaceutically acceptable acid addition salt thereof, wherein X is —CH$_2$— or —CO—, and when R is not bonded to R$_1$, Y is 0 or S, R is methylene or di-, tri-, tetra-, penta- or hexa-methylene, unsubstituted or substituted by one or more alkyl radicals having from 1 to 4 C atoms; and R$_1$ is alkyl having from 1 to 4 C atoms, unsubstituted or substituted by alkoxy having from 1 to 4 C atoms, cycloalkyl, cycloalkylmethyl or cycloalkylethyl having from 3 to 6 C atoms in the cycloalkyl moiety, phenyl, benzyl, furyl, furylmethyl, pyranyl, pyranylmethyl, thienyl, thienylmethyl, tetrahydrofuryl, tetrahydrofurylmethyl or pyridyl, or when R is bonded to R$_1$,

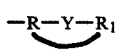

together represent furyl, tetrahydrofuryl, chlorofuryl, bromofuryl, methylfuryl, pyranyl or morpholinyl.

2. A compound according to claim 1 in which R is methylene or di-, tri-, tetra-, penta- or hexa-methylene, unsubstituted or substituted by one or more alkyl radicals having from 1 to 4 C atoms.

3. A compound according to claim 2 wherein said one or more alkylradicals have 1 or 2 C atoms.

4. A compound according to claim 1 in which R$_1$ is alkyl having from 1 to 4 C atoms, unsubstituted or substituted by alkoxy having from 1 to 4 C atoms, cycloalkyl, cycloalkylmethyl, or cycloalkylethyl having from 3 to 6 C atoms in the cycloalkyl moiety, phenyl, benzyl, furyl, furylmethyl, pyranyl, pyranylmethyl, thienyl, thienylmethyl, tetrahydrofuryl, tetrahydrofurylmethyl or pyridyl.

5. A compound according to claim 1, in which

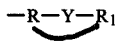

together represent furyl, tetrahydrofuryl, chlorofuryl, bromofuryl, methylfuryl, pyranyl or morpholinyl.

6. A compound according to claim 1 in which when R is not bonded to R$_1$, R is methylene, ethylene or trimethylene, unsubstituted or substituted by from 1 to 3 methyl groups, Y is 0 or S, and R$_1$ is alkyl having from 1 to 4 C atoms, optionally substituted by methoxy or ethoxy, or phenyl, or when R is bonded to R$_1$,

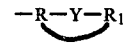

together represent furyl-2-, or 5-methyl-, 5-chloro- or 5-bromo-furyl-2-, or thien-2-yl, or 5-methyl-, 5-chloro- or 5-bromo-thien-2-yl.

7. A compound of claim 1 which is 1-N-[2-Methoxyethyl]-sisomicin and its pharmaceutically accepted acid addition salts.

8. A compound of claim 1 which is 1-N-[2-Ethoxyethyl]-sisomicin and its pharmaceutically accepted acid addition salts.

9. A comound of claim 1 which is 1-N-[2-(2-Methylthio)propyl]-sisomicin and its pharmaceutically accepted acid addition salts.

10. A compound of claim 1 which is 3″-N-[2-(n-Butoxy)-ethyl]-sisomicin and its pharmaceutically accepted acid addition salts.

11. A compound of claim 1 which is 1-N-[2-(i-Propoxy)ethyl]-sisomicin and its pharmaceutically accepted acid addition salts.

12. A compound of claim 1 which is 1-N-[2-(2,2-Dimethyl-2-methoxy)-ethyl]-sisomicin and its pharmaceutically accepted acid addition salts.

13. A compound of claim 1 which is 1-N-[2-Methoxyacetyl]-sisomicin and its pharmaceutically accepted acid addition salts.

14. A compound of claim 1 which is 6′-N-[3-Ethoxyacetyl]-sisomicin and its pharmaceutically accepted acid addition salts.

15. A compound of claim 1 which is 1-N-[2-Methylthioacetyl]-sisomicin and its pharmaceutically accepted acid addition salts.

16. A compound according to claim 1 which is in the form of a pharmaceutically acceptable acid addition salt.

17. A pharmaceutical composition containing as an active ingredient an effective amount of a compound according to claim 1 in admixture with a solid or liquefied gaseous diluent or in admixture with a liquid diluent other than a solvent of a molecular weight less than 200 except in the presence of a surface-active agent.

18. A pharmaceutical composition containing as an active ingredient an effective amount of a compound according to claim 1 in the form of a sterile or isotonic aqueous solution.

19. A composition according to claim 17 containing from 0.5 to 95% by weight of the said active ingredient.

20. A medicament in dosage unit form comprising an effective amount of a compound according to claim 1 together with an inert pharmaceutical carrier.

21. A medicament of claim 20 in the form of tablets, pills, dragees, capsules, ampoules, suppositories, ointments, creams or lotions.

22. A method of combating bacterial infection in a warm-blooded animal which comprises administering to the said animal an effective amount of an active compound according to claim 1 either alone or in admixture with a diluent or in the form of a medicament.

23. A method according to claim 22 in which the active compound is administered in an amount of from 1 to 15 mg per kg body weight from 2 to 4 times per day, parenterally.

24. A method according to claim 22 in which the animals are ruminants.

25. A method according to claim 22 in which the active compound is administered orally.

26. A method according to claim 22 in which the active compound is administered topically.

27. A method according to claim 26 in which the active compound is administered in the form of an ointment, cream or lotion containing from about 0.1 to 3% w/v of active ingredient, from 2 to 5 times per day.

28. An animal feed containing a compound according to claim 1.

* * * * *